(12) United States Patent
Sivavec et al.

(10) Patent No.: US 6,491,828 B1
(45) Date of Patent: Dec. 10, 2002

(54) METHOD AND SYSTEM TO REMOTELY MONITOR GROUNDWATER TREATMENT

(75) Inventors: Timothy Mark Sivavec, Clifton Park, NY (US); Patricia Denise Mackenzie, Clifton Park, NY (US); Sunita Singh Baghel, Rensselaer, NY (US); Joseph James Salvo, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 7 days.

(21) Appl. No.: 09/708,984

(22) Filed: Nov. 7, 2000

(51) Int. Cl.[7] .................................................. C02F 1/00
(52) U.S. Cl. ........................... 210/739; 95/8; 95/25; 95/149; 95/245; 96/156; 96/244; 166/53; 166/167; 210/85; 210/96.1; 210/170; 210/188; 210/747
(58) Field of Search .................... 210/85, 96.1, 143, 210/170, 258, 259, 263, 266, 188, 650, 662, 663, 669, 739, 747, 805, 806; 166/53, 75.11, 267, 370; 175/50; 96/10, 156, 214; 95/8, 215, 90, 149, 243, 245; 405/52

(56) References Cited

U.S. PATENT DOCUMENTS

| | | | |
|---|---|---|---|
| 4,727,936 A | | 3/1988 | Mioduszewski et al. ...... 166/53 |
| 4,830,757 A | * | 5/1989 | Lynch et al. ................ 210/96.1 |
| 4,839,061 A | * | 6/1989 | Manchak et al. ............ 210/170 |
| 4,844,807 A | * | 7/1989 | Manchak et al. ............ 210/170 |
| 5,116,515 A | * | 5/1992 | Selsesnick .................. 210/747 |
| 5,122,165 A | * | 6/1992 | Wang et al. ................. 210/170 |
| 5,126,050 A | * | 6/1992 | Irvine et al. |
| 5,316,085 A | | 5/1994 | Dawson et al. ............. 210/747 |
| 5,399,267 A | * | 3/1995 | Wang et al. |
| 5,468,088 A | | 11/1995 | Shoemaker et al. .......... 166/53 |
| 5,639,380 A | | 6/1997 | Misquitta .................... 210/747 |
| 5,646,863 A | * | 7/1997 | Morton ......................... 210/85 |
| 5,804,743 A | | 9/1998 | Vroblesky et al. ....... 73/863.23 |
| 5,813,798 A | * | 9/1998 | Whiffen ...................... 210/739 |
| 5,954,452 A | | 9/1999 | Goldstein .................... 422/121 |
| 5,996,423 A | | 12/1999 | Baghel et al. ........... 73/863.23 |
| 6,021,664 A | * | 2/2000 | Granato et al. ............. 210/170 |
| 6,098,448 A | | 8/2000 | Lowry et al. ................... 73/38 |

* cited by examiner

Primary Examiner—Joseph W. Drodge
(74) Attorney, Agent, or Firm—Toan P. Vo; Noreen C. Johnson

(57) ABSTRACT

A contaminated aqueous composition is withdrawn from a groundwater extraction well and the groundwater is treated in a pump and treat system to remove a contaminant. The treating of the aqueous composition is monitored from a location remote from the groundwater extraction well and the treating is adjusted to remove a contaminant in accordance with the monitoring. A system to treat a contaminated aqueous composition comprises a capture zone to intercept a contaminated aqueous composition and a surface pump and treat system to receive and treat the contaminated aqueous composition from the capture zone. The system also includes a sensor that senses a contaminant in the contaminated aqueous composition and a monitor to receive information concerning the contaminant from the sensor and to consequently control the pump and treat system to treat the contaminated aqueous composition. The monitor is situated at a location remote from the pump and treat system.

33 Claims, 5 Drawing Sheets

METHOD AND SYSTEM TO REMOTELY MONITOR GROUNDWATER TREATMENT

BACKGROUND OF THE INVENTION

The invention relates to a method and system for remote monitoring of groundwater. In particular, the invention relates to remote monitoring of a pump and treat method at a remediation site.

Contaminants from a pollutant source can contact a groundwater aquifer to form a groundwater contaminant plume. The plume can migrate in the direction of groundwater flow. A pump and treat method can be used to provide remediation of the plume-containing aquifer. Pump and treat operates by intercepting the groundwater at a capture zone, pumping the groundwater from the capture zone to the surface, removing the contaminant in a surface remediation unit and then either recharging the treated water back into the ground or discharging it to a surface water body or municipal sewage plant. Once the groundwater has been pumped to the surface, contaminants can be removed to very low levels with established remediation technologies or combinations of established technologies. Examples of commonly applied surface remediation technologies include air stripping, carbon adsorption, oil-water separation, chemical oxidation, membrane filtration, metals precipitation/adsorption and ion exchange.

Pump and treat is an accepted remediation technology however it involves high equipment and labor costs. Efforts to improve pump and treat have focused on control in two distinct phases—an in situ phase during migration to or at the capture zone and the remediation phase after pumping to the surface. The two phases involve different considerations. It would be advantageous to closely monitor a pump and treat system to assure process effectiveness and regulatory compliance. Further it would be advantageous to provide monitoring that would assure that cost saving from effective monitoring was not dissipated by the cost of monitoring itself. Thus far, effective pump and treat system monitoring has been limited to control of the first in situ phase. For example, Misquitta, U.S. Pat. No. 5,639,380 discloses monitoring an extraction well for the purpose of controlling groundwater hydrodynamics. In the Misquitta process, groundwater is extracted from a well at a first flow rate, hydrodynamics of the surrounding area are monitored and the hydrodynamic information is transmitted to a computer controller, which computes a new second flow rate and automatically adjusts a pump to the second flow rate to maintain a desired capture zone. Similarly, Dawson, U.S. Pat. No. 5,316,085 discloses providing liquid level sensing means within a wellbore. A pump controls the liquid level in response to the sensing means. Lowry et al., U.S. Pat. No. 6,098,448 discloses determining permeability, i.e. soil conductivity to fluid flow.

These monitoring patents are limited to sensing water pressure or hydrodynamics in the vicinity of a well for the purpose of adjusting flow. While this is an important consideration in controlling a pump and treat system, equally if not more important considerations relate to control of the surface treatment step. Control of the surface treatment step may depend on the nature and extent of the contaminant in either or both of the feed groundwater from the capture zone and product water from the treatment facility. Detection of the nature and extent of a contaminant depends upon timely testing of representative samples and the ability of a sampling system to representatively capture the contaminant of interest.

Conventional remediation site monitoring, diagnostics, and reporting are expensive and labor intensive operations. Yearly costs for remediation site monitoring, diagnosing and reporting often exceed over $2000 per well. Conventional remediation site monitoring, diagnosing and reporting methods and systems comprise providing a well or other access means for groundwater at a remediation site. A person visits the remediation site, locates the well, and accesses the well. The groundwater in the well is sampled for characteristics (hereinafter "groundwater characteristics"), such as, but not limited to, water quality parameters; groundwater level; and contaminants such as benzene, toluene, ethyl-benzene, xylenes (BTEX), aromatic hydrocarbons and chlorinated solvents such as trichloroethylene (TCE), tetrachloroethylene (PCE) and their degradation products, dichloroethylene and vinyl chloride in the groundwater. The groundwater sample is then transported to a laboratory, often remote from the remediation site. The sample is then analyzed for certain characteristics by appropriate methods. Costs are associated with each step and the costs are often high depending on the well's location with respect to the laboratory. Exact costs are remediation site dependent, reflecting a complexity of an analysis to be performed. Real-time data for the groundwater is desirable. The transportation of the sample from the well to the laboratory takes time. Further, time delays are associated with the analysis of the groundwater sample.

There is a need first, for monitoring, diagnosing and reporting properties of effluents to or from a pump and treat treatment zone and second, for a system and process to accurately sample the effluents of a pump and treat process and system.

BRIEF SUMMARY OF THE INVENTION

The present invention provides a method and system to monitor a groundwater pump and treat system and to use the information acquired by the monitoring to control the system. In the method, a contaminated aqueous composition is withdrawn from a groundwater extraction well and the groundwater is treated in a pump and treat system to remove a contaminant. The treating of the aqueous composition is monitored from a location remote from the groundwater extraction well and the treating is adjusted to remove a contaminant in accordance with the monitoring.

In another embodiment, the invention relates to a system to treat a contaminated aqueous composition. The system comprises a capture zone to intercept a contaminated aqueous composition and a surface pump and treat system to receive and treat the contaminated aqueous composition from the capture zone. The system also includes a sensor that senses a contaminant in the contaminated aqueous composition and a monitor to receive information concerning the contaminant from the sensor and to consequently control the pump and treat system to treat the contaminated aqueous composition. The monitor is situated at a location remote from the pump and treat system.

DETAILED DESCRIPTION OF THE INVENTION

Figure 1:
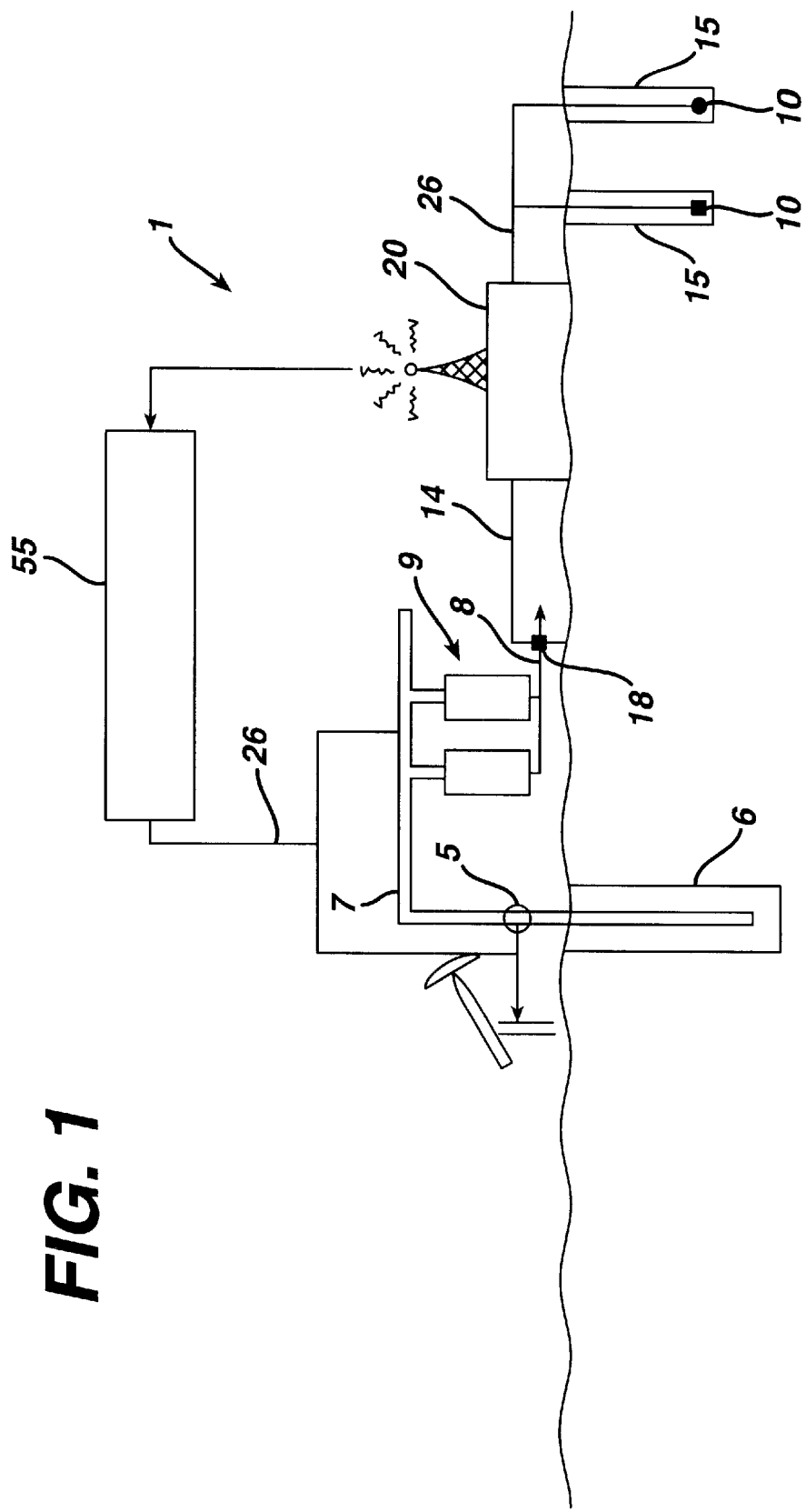
FIG. 1 is a schematic illustration of a remotely monitored pump and treat system.

The invention provides a method and system to monitor and control pump and treat operations for groundwater remediation. Specific elements of the system can include a sensor to detect contaminants in groundwater such as dissolved-phase chlorinated solvents, hydrocarbons, metals, LNAPL and DNAPL. A flow-through cell can be provided to hold the sensor and to expose the sensor to the groundwater, a transceiver to send a data signal from the sensor to a collector such as a data collection station (via modem, radio or satellite), a data transmission system and a controller including a data processing and report formatting site.

The method and system of the invention can provide real-time monitoring to allow site operators to fine-tune the operation of pumping wells or to automatically adjust the pumping wells without operator intervention, to select operating wells at a site and to feed pumped groundwater to pre-selected treatments. Presently, pump and treat systems are designed based on available field data and are monitored perhaps four times per year. The method and system can provide frequent data on contaminant concentration, which can be used to optimize the groundwater extraction for a more efficient treatment. Improved data collection in an early remedial investigation phase can insure appropriate sizing of a pump and treat system.

Contaminant concentration data can be used to direct contaminated groundwater to an appropriate treatment. For example, if the concentration of a petroleum hydrocarbon phase in groundwater decreases to the point that it can not be treated by an oil-water separator, the invention can be used to detect the decrease and to send the groundwater directly to a carbon bed. In the same way, if groundwater pumped to the surface has an acceptable contaminant level, it can be directed away from treatments and directly discharged. The invention can obviate field operators and can be used to directly transmit a groundwater sample to an analytical laboratory or to obviate the analytical laboratory submission altogether.

The invention can provide increased data density to permit facilitate trend analysis for site models. The invention can also increase the quality of the data. Coupling of monitors for precipitation (e.g., rainfall) and groundwater elevation to pump and treat monitoring can provide a further benefit. The invention can provide for automatically altering extraction rates in accordance with changes in groundwater elevation.

The remote monitoring method and system can provide real-time data. The real-time data can be analyzed at the remediation site so that prompt action can be taken to address particular characteristics of an aqueous composition. Herein, the term "aqueous composition" includes water environments, particularly natural water environments such as aquifers, particularly groundwater and other subsurface environment. The invention relates to remote control of a pump and treat system for removing contaminants from an aqueous composition. Pump and treat operates by intercepting groundwater at a capture zone, pumping the groundwater from the capture zone to the surface, removing the contaminants in a surface remediation unit and then either discharging the treated water back into the ground or discharging it to a surface water body or municipal sewage plant. Remote means separated by an interval in space that is greater than a usual separation between a data center controlling a pump and treat method. Remote means off-site and separated by a distance at least greater than a distance between monitored wells.

These and other features will become apparent from the drawings and following detailed discussion, which by way of example without limitation describe preferred embodiments of the present invention.

FIG. 1 shows an overall system and process of the invention, which will be described in more detail in reference to FIGS. 2 to 5. FIG. 1 shows remediation site monitoring system 1, which includes monitoring wells 15 including probe and sensing modules 10. Contaminated groundwater is pumped via pump 5 from collection well 6, which is shown separate from monitoring wells 15. However in other embodiments, the collection well can be one or more of the monitoring wells 15 with an emplaced monitoring module 10.

The contaminated groundwater is conveyed 7 to treating unit 9, which is shown as double adsorption units. The combination of the pump 5, well 6 and treatment unit 9 can include any method and system for withdrawing contaminated water from a well and treating the water. For example, the contaminants can be volatilized in an air stripping tower or vapor phase contaminants can be adsorbed onto granular activated carbon (GAC). The groundwater is treated in the unit 9 and is discharged via line 8.

Collector 20 is a data collection center that receives groundwater contaminant information from modules 10 via line 26, which can represent a signal transmitted from a module 10 as hereinafter described. Additionally, collector 20 can receive data relating to the extent of treatment in unit 9 via connection 14 from an appropriate sensing unit 18. Communication link 30 transmits data collected at collector 20 to a remote controller 55. Remote controller 55 can analyze the data and control the operation of either or both pump 5 and treatment unit 9 accordingly.

Figure 2:
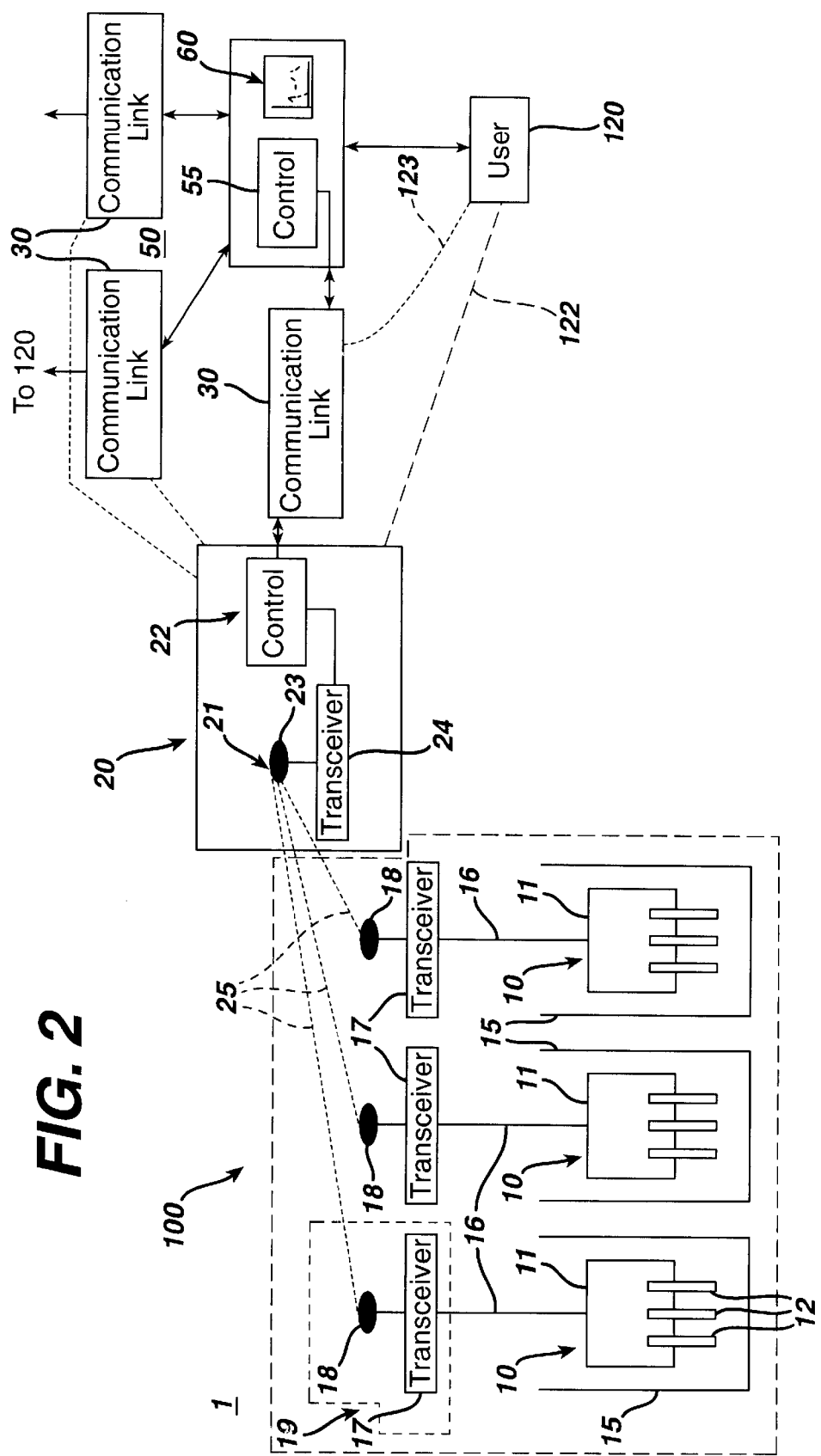
FIG. 2 is a schematic representation of a monitoring system.

The monitoring system 1 is schematically illustrated in FIG. 2. The monitoring system 1 comprises a well module (module) 10. The module 10 comprises a probe 11 and at least one sensor 12 disposed on the probe 11. FIG. 2 illustrates three such sensors 12. The module 10 includes any number of sensors 12 whereby desired groundwater characteristics can be readily determined.

The module 10 is disposed in groundwater wells 15 at a remediation site 100. Groundwater wells 15 can include private drinking water wells, municipal drinking water wells, pollution control wells and landfill monitoring wells. The wells 15 can be spread throughout a remediation site 100 or over a larger or smaller area, for example disposed in varying altitudes to determine groundwater flow characteristics. Module 10 can sense various groundwater characteristics such as water quality, groundwater level and contaminant and impurity content. The module 10 can generate signals (data) corresponding to one or more of the groundwater characteristics. The module 10 includes a communications unit 19, which is electronically coupled and capable of transmitting data to a collector such as a data collection center 20. The communications unit 19 includes a well transceiver 17 to which signals from the module 10 are communicated to data collection center 20. The signals can be communicated from well transceiver 17 by a hardwired communication connection such as an electrical conductor 16; by a wireless communication connection such as by radio signals, by satellite communications or by combinations of wireless and hardwired connections. The communications unit 19 can comprises an antenna 18 that is connected to the transceiver 17. The transceiver 17 transmits information in the form of signals 25 representative of the data from the communications unit 19 to data collection center 20.

The data collection center 20 comprises a center communications unit 21 that can receive signals 25 from the transceiver 16. The center communications unit 21, which is similar to the communications unit 19, can comprise an antenna 23 and a transceiver 24. If more than one well is located at the remediation site 100, the center communications unit 21 can receive signals 25 from a plurality of wells 15. The data collection center 20 also comprises a controller 22 that analyzes the signals 25 and typically generates information concerning the groundwater characteristics. The controller 22 of the data collection center 20 can include a "user friendly" data acquisition software package. The software package in the controller 22 transforms information into easy to read real or virtual formats or into commands to control treating unit 9 shown in FIG. 1.

The information transmitted to the data collection center 20 contains data representative of the groundwater characteristics. The information can be collected and stored at the data collection center 20. The information can be accessed by a user, regardless if the user is located at the data collection center 20 or remotely located. The information format structure can be customized by the user, where the user formats a desired information structure in a report dependent on the intended use of the information. The information is formatted to interpret, classify, quantify, and categorize the groundwater characteristics. For example, an information report can provide real-time information concerning groundwater characteristics. The information report can also be formatted to provide a historical summary for the groundwater characteristics of the individual wells 15 and the remediation site 100.

The data collection center 20 can be located proximate a well 15. For example, the data collection center 20 can be located at the remediation site 100 within range of the communication unit 19. Alternatively, the data collection center 20 can be located proximate one or more remediation sites. In an alternative, the data collection center 20 can be mobile and can be moved within range of the communication unit 19 to receive data. The location of the data collection center 20 can be anywhere within range of the communication unit 19.

The controller 22 comprises any appropriate solid-state device, for example a computer. The control center 22 may include data acquisition capability, such as data acquisition software. A controller 22 can comprise a central processor for overall, system-level control, and separate sections to perform various different specific combination functions and other processes under control of the central processor section. The controller 22 can be implemented using a variety of separate dedicated, programmable integrated and other electronic circuits or devices. These devices include hardwired electronic, logic circuits including discrete element circuits and programmable logic devices. The programmable logic devices include a programmable logic device (PLD), programmable array logic (PAL), programmable logic array (PLA) and the like. The controller can also be implemented using a suitably programmed general-purpose computer such as a microprocessor, microcontrol or other processor device such as a control processing unit (CPU) or microprocessing unit (MPU) in conjunction with one or more peripheral data and signal processing devices. Any finite state machine capable of implementing flow charts can be used as the controller.

The controller 22 can print hard copies of reports and provide computer readable electronic output, which can be accessed by a user 130 monitoring groundwater characteristics. If the user 120 is located at a central hub monitoring site 50 (hereinafter "monitoring site") remote from the remediation site 100, the user can access electronic information relating to the remediation site 100 via a communications link. The user 120 can connect to the data collection center 20 via the monitoring site 50, as illustrated by the solid line 121 in FIG. 2. Alternatively, the user 120 can connect to the data collection center 20 directly, as illustrated by the dashed line 122. As another alternative, the user 120 can connect to the data collection center 20 through the communications link 130 as illustrated by dotted line 123. Moreover, a plurality of users can connect to the monitoring site 50 for data from the data collection center 20 through respective communications links 130.

A monitoring site user 120 can receive electronic information from a plurality of remediation sites. The monitoring site 50 communicates with each data collection center 20 through a communication link 30. The site 50 can communicate with a plurality of data collection centers 20. The communication link 20 can be a phone modem, network connection, communication, radio communication or other wireless communication system or a cellular communication, satellite communication, web access communication or Internet access communication or combinations thereof. The particular construction of the communication link 30 depends on communication link types accessible at the data collection center 20, to the remediation site 100 or to the user at the monitoring site 50. The user can access and readily determine groundwater characteristics from any location via the communication link 30.

The monitoring site 50 can be located centrally or anywhere a user can have access to the communication link 30. For example, a user can have access via a network hook-up. The monitoring site 50 can comprise a controller 55, similar to controller 22. The controller 55 can include a "userfriendly," data acquisition software package. Such a software package can transform information into a formatted report. The report can include a plot, graph, table, spreadsheet or the like. The report can be electronically available to the user or can be printed as a hard copy. A user can specify a report format and remotely obtain the formatted report from the data collection center 20 via communications link 30.

Figure 3:
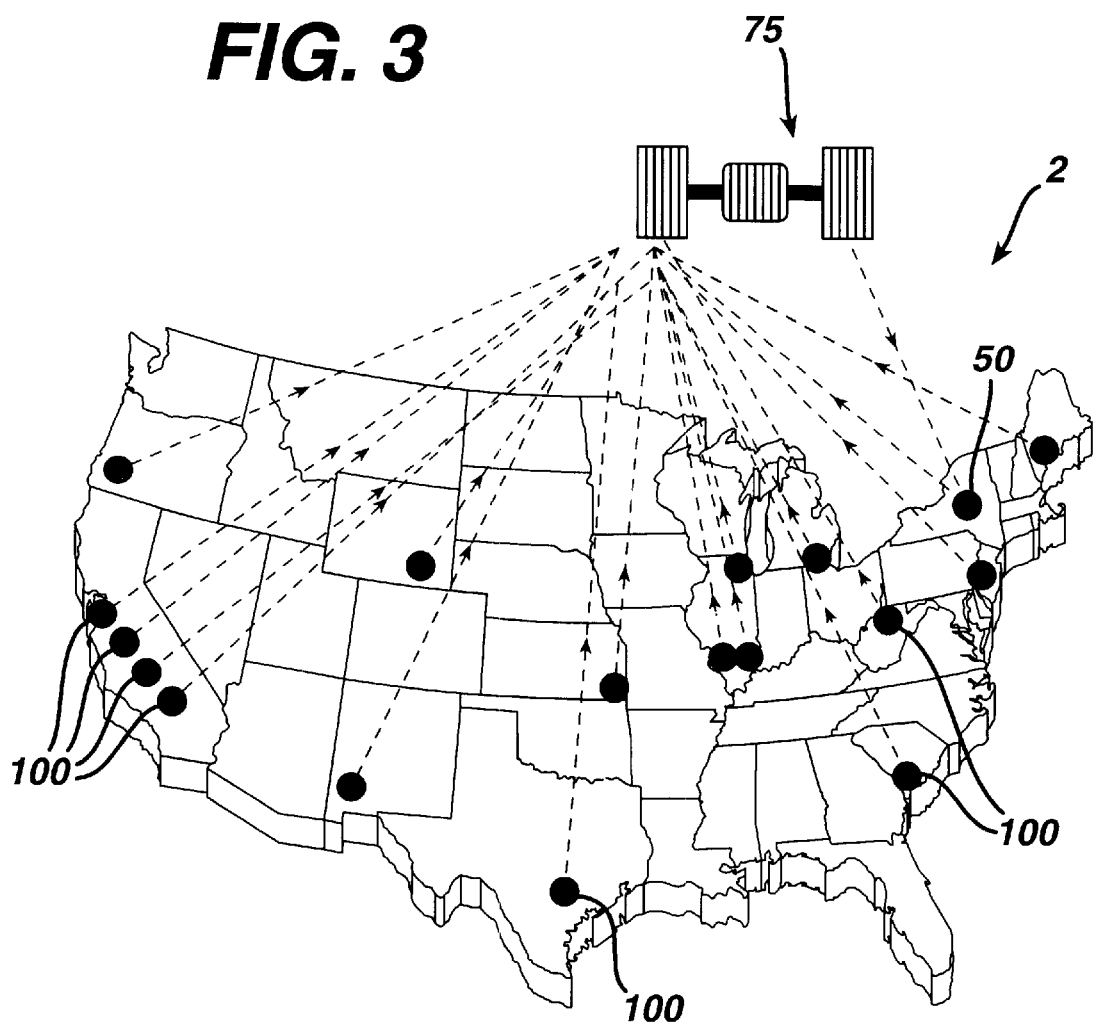
FIG. 3 is an illustration of a system for collection from remediation sites throughout the United States.

Monitoring site 50 is capable of collecting information from remediation sites throughout the country. The monitoring site 50 can be located in a range between a relatively short distance from the data collection center 20, such as less than about 10 meters, or can be located a remote long distance removed from the center 20 depending on the range of a communication unit 19. FIG. 3 is an illustration of a communications network system 2 for collecting information from remediation sites 100 throughout the United States. A satellite 75 can be positioned in geosynchronous orbit over the United States. FIG. 3 illustrates a single satellite 75 but can represent a plurality of satellites. Information can be directed to a monitoring site 50 by reflecting a signal off a satellite, similarly collecting and re-transmitting signals or by any other method accessible by a network type connection.

The monitoring system 1 can provide both historical and real-time information that is accessible by a user. A user does not require knowledge of specific programs, routines or software to access the information because a report can be provided in a format of the user's choosing. Connectivity among any of the communications unit 19 software, data collection center 20 software, communications unit 21 software, communication link 30, monitoring site controller 50 or user access software can be provided by a linking platform. Reports can be provided that are usable, understandable and manipulatable. A report format can provide real-time information or historical trend data of groundwater and groundwater characteristics. The real-time information permits quicker response to undesirable groundwater conditions such as contaminant increase.

The sensor 12 can detect the groundwater contaminant of interest or a contaminant level of interest. The sensor 12 can be provided in the probe 11 for particular contaminants. Suitable types of sensor 12 include a chemical sensor, fiber optics sensor, solid-state sensor such as a metal oxide semiconductor (MOS), an electrochemical sensor and combinations of such sensors.

Figure 4:
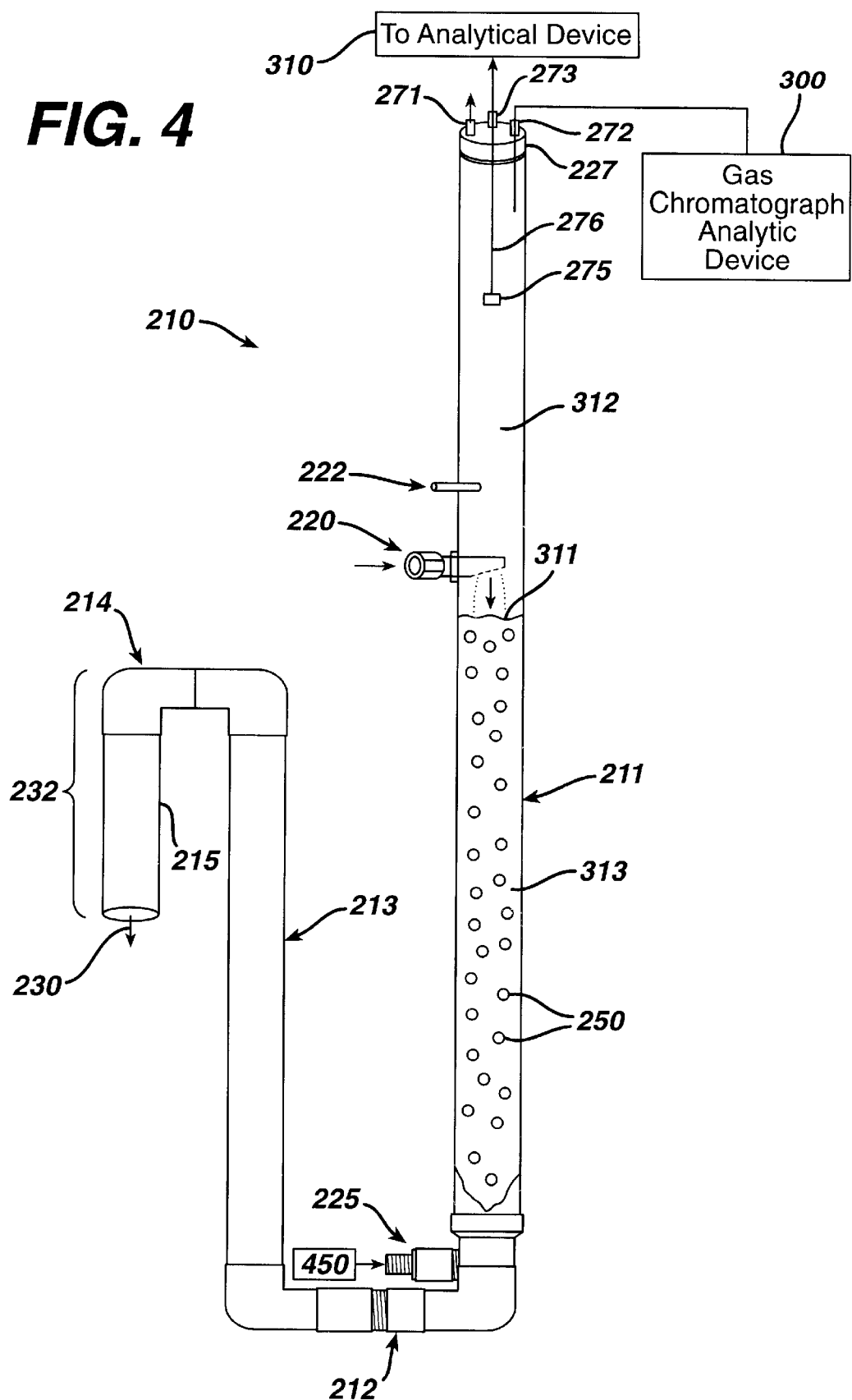
FIG. 4 is a schematic part-sectional illustration of an exemplary on-line sparging, sampling and monitoring system.

FIG. 4 is an illustration of a preferred on-line sampling and sensing system 210 that can serve as module 10 in the monitoring system 1 of FIG. 2. In FIG. 4, on-line sampling and sensing system 210 includes a network of interconnected tubular members for transporting discharge for monitoring. The on-line sampling and sensing system 210 comprises a sparger tubular member 211, a bottom connector tubular member 212, a side tubular member 213, a P-trap tubular member 214 and a venting and discharge tubular member 215. The tubular members and connections in the on-line sampling and sensing system 210 can be configured with dimensions that are sufficient to reduce or eliminate fouling and blockage by sediments or particulates.

Sparger tubular member 211 comprises a cap 227 at one end opposite connecting tubular member 212 at the other end. The cap 227 comprises a plurality of ports for on-line sparging sampling and sensing system components. The cap exhaust port 271 may be vented, connected to an exhaust treatment system or connected to a condensing system. In FIG. 4, the cap 227 comprises a cap exhaust port 271 for venting pressure in the sparger tubular member 211 to the atmosphere. The cap 227 also comprises a gas chromatography port 272 that permits gas chromatography of a headspace in the on-line sparging sampling and sensing system 210. For example, the sparger tubular member 211 can include a micro-gas chromatographer (micro-gc). Further, the cap 227 comprises a sensor port 273 that includes a sensor lead 276 that extends from a sensor 275, such as a metal-oxide semiconductor (MOS) sensor and that can be connected with an analytic device.

Sparger tubular member 211 also includes an inlet 220 for feeding influent. The inlet 220 is disposed in the network of tubular members and is positioned in between the cap 227 and a connection of the sparger tubular member 211 to the bottom connector tubular member 212. The inlet 220 can provide a waste and by-product passage for a process being monitored or inlet 220 can be connected to the waste and by-product passage by a fluid connection for withdrawing a representative sample of the waste and by-product. The influent aqueous discharge establishes an aqueous discharge level 311. A headspace 312 is defined above the aqueous discharge level 311. Sparged materials, such as VOCs, can be monitored in the headspace 312. The aqueous discharge level 311 defines an aqueous discharge portion 313 for sparging, as discussed hereinafter.

Further, the sparger tubular member 211 comprises a gas inlet 222, which is positioned above the inlet 220 disposed between inlet 220 and cap 227. Gas inlet 222 permits inert gas, such as ambient air to enter the sparger tubular member 211. Thus, the on-line sparging sampling and sensing system 210 may have equalized pressures during flow without back pressure or vacuum. Inert gas inlet 222 can be disposed above the aqueous discharge level 311. This positioning facilitates removal of VOCs from headspace 312. The sparger tubular member 211 also includes a sparger 225, which is disposed close to connection of the sparger tubular member 211 to bottom connector tubular member 212. Sparger 225 permits inert non-reactive gas 250 to continuously flow through aqueous discharge portion 313. The gas introduced into the sparger 225 is inert to avoid reaction with VOCs or other materials in the aqueous discharge. Exemplary gases that can be introduced into the on-line sparging sampling and sensing system 210 at the sparger 225 include air and nitrogen.

The tubular members of the on-line sparging sampling and sensing system 210 comprise any appropriate material for fluid flow in which the materials will not be degraded, corroded, or otherwise adversely affected by the aqueous discharge. For example, the tubular members may comprise polyvinyl chloride (PVC) or other non-reactive inert materials such as thick-walled glass or acrylic and other clear chemically resistant polymer resins that allow visual inspection.

The aqueous discharge level in the on-line sparging sampling and sensing system 210 can be controlled at a level by the P-trap tubular member 214 and venting and discharge tubular member 215. The venting and discharge tubular member 215 comprises a vent to the atmosphere, which is generally illustrated as 230, located at some point along the on-line sparging sampling and sensing system 210 above the aqueous discharge flow path. Vent 232 provides atmospheric pressure and relief to the on-line sparging sampling and sensing system 210.

Analytic devices, 300 and 310 that are connected to the on-line sparging sampling and sensing system 210 can be selected from a variety of available process analyzers. For example, a MOS sensor 275 and micro-gas chromatograph coupled between headspace 312 and analytic devices 300 and 310 can provide near real-time monitoring and analyzing. The term "real-time" means a processing system that controls an ongoing process and delivers its outputs or controls its inputs not later than the time when these are needed. For example, the MOS sensor 275 can deliver total hydrocarbon concentration data at response times of about 1 second. Further, a micro-gas chromatography system can provide VOC data at a response time of about 6 minutes.

Figure 5:
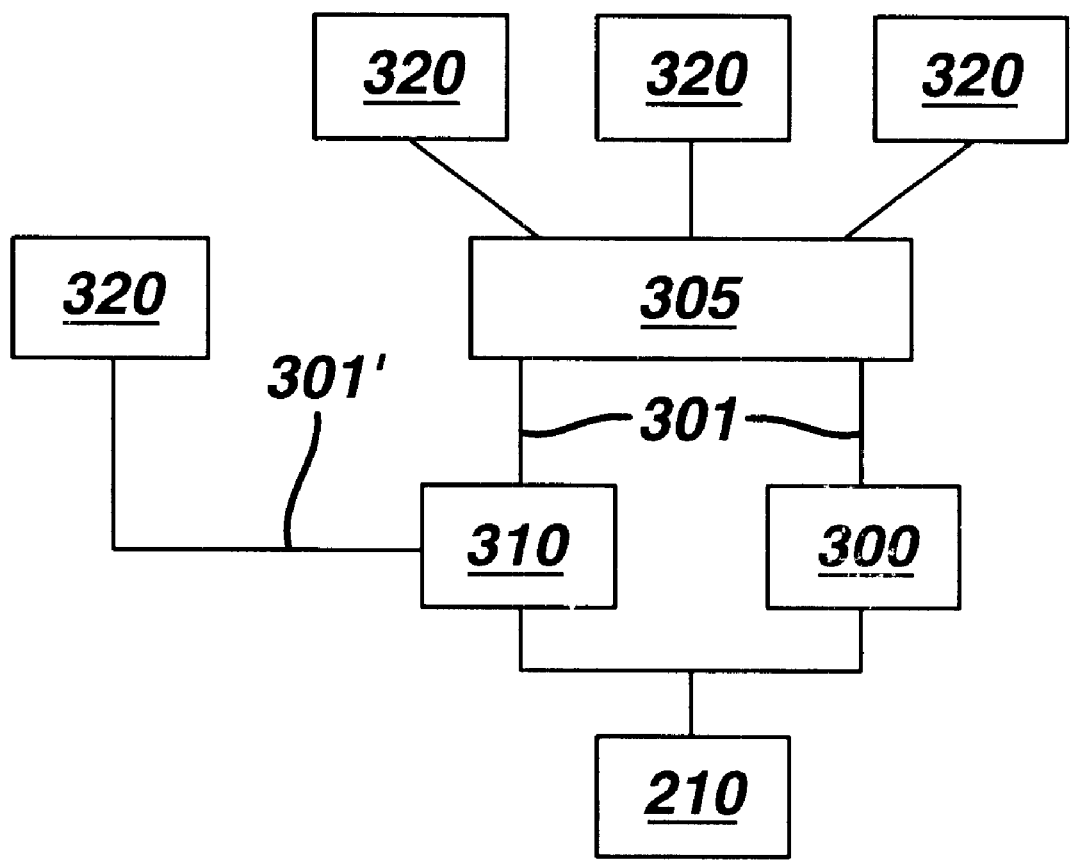
FIG. 5 is a block diagram of the on-line sparging sampling and sensing system.

The on-line sparging sampling and sensing system 210 can be connected to communication link to provide analyzed data to a user or remote controller. For example, FIG. 5 illustrates a block diagram of the on-line sparging sampling and sensing system 210 connected to various users 320 via communication links 301. The users 320 can be associated with the controller 22 of FIG. 2 or can actually be the controller 22 in the instance of automated remote control of the treating unit 9 shown in FIG. 1. Information from the analytic devices can be transferred directly to a party, for example by communication link 301'. Alternatively, information from the analytic devices 310 or 300 can be transferred directly to a party by communication links 301 that lead to a common data gathering location 305, such as a network location. The communication links 301 can be a phone modem, network connection, radio communication and other wireless communication, cellular communication, satellite communication, web access communication, Internet communication or combinations thereof.

Referring again to FIG. 2, each transceiver 17 and 24 of communications units, 19 and 21, can comprise an appropriate device that receives and sends electric signals. Each antenna 18 and 23 (provided unless each transceiver is hardwired) can comprise an integrated receiver and transmitter antenna. Alternatively, an antenna comprises a separate element from its transceiver. Each transceiver can be a low (few volts) power consumption transceiver unit that requires little human interaction. For example, each transceiver can use a self-contained power source, such as a battery pack, solar-power or solar-power re-charged battery. Transceiver 17 can operate without user interaction Transceiver 17 is a device that withstands environments of the groundwater well and remediation site. The transceiver 17 can comprise a radio and RF device that provides coverage over an intended geographical range. The transceiver 24 may require more power than the transceiver 17 since it may communicate over longer distances through the communication link 30.

The communication link 30 can provide two-way communication between a user 320 (which can be controller 22) and the module 10. The two-way communication can allow remote monitoring system calibration by a user without traveling to a site. Also, the two-way communication permits automatic selection, activation and de-activation, modification, fine-tuning, manipulation of treating unit 9. The two-way communication van be provided by any appropriate communication mode such as radio, satellite, facsimile, hardwired communication, voice mail, alarm, mail, Internet transmission or combinations thereof.

The monitoring system 1 of the invention can reduce labor costs and errors associated with sampling the well 15. The monitoring system 1 can eliminate sample disposal and associated hazardous material issues and can eliminate transportation cost of samples for analysis and chain of custody issues relating to contamination sources. Further, the monitoring system 1 substantially eliminates external analytical lab services and reduces contamination from remediation site traffic.

While preferred embodiments of the invention have been described, the present invention is capable of variation and modification and therefore should not be limited to the precise details of the Examples. The invention includes changes and alterations that fall within the purview of the following claims.

What is claimed is:

1. A method of treating a contaminated aqueous composition, comprising:
   withdrawing said contaminated aqueous composition from a groundwater extraction well of a pump and treat system;
   treating said contaminated aqueous composition to remove a contaminant in said contaminated aqueous composition to a lower concentration than a concentration of said contaminant in said contaminated aqueous composition, thereby producing a treated aqueous composition;
   monitoring in real time said treating of said contaminated aqueous composition from a location remote from said groundwater extraction well by sensing a characteristic of said contaminant in said contaminated aqueous composition; and
   adjusting in real time said treating in response to said real-time monitoring to remove said contaminant from said contaminated aqueous composition to said lower concentration.

2. The method of claim 1, further comprising:
   sparging a non-reactive gas into said contaminated aqueous composition to separate a volatile contaminant; and
   monitoring said volatile contaminant from said aqueous composition.

3. The method of claim 1, wherein said sensing a characteristic of said contaminant in said contaminated aqueous composition comprises:
   diffusing said contaminant from said contaminated aqueous composition through a membrane to separate said contaminant from said composition; and
   determining said characteristic of said separated contaminant.

4. The method of claim 1, wherein said contaminated aqueous composition comprises groundwater and said method further comprises:
   intercepting said ground water at an underground capture zone, pumping the groundwater from the capture zone to ground surface and treating said groundwater by removing said contaminant in a surface remediation unit, thereby producing a treated groundwater.

5. The method of claim 4, further comprising recharging said treated groundwater back into the underground, discharging said treated groundwater to a surface water body or discharging said treated groundwater to a municipal sewage plant collector.

6. The method of claim 1, wherein said monitoring comprises sampling said aqueous composition.

7. The method of claim 6, wherein said sampling comprises sparging a volatile organic compound from said aqueous composition and sensing said volatile organic compound.

8. The method of claim 6, wherein said sampling comprises
   providing a network of tubular members that are interconnected to each other to define a fluid passage and a sparger disposed within said passage;
   flowing aqueous composition within the vicinity of said sparger;
   causing a gas from said sparger to flow through said aqueous composition to sparge a volatile organic compound and to convey said volatile organic compound to a forming headspace;
   sensing said volatile organic compound within said headspace to determine a volatile organic compound content of said contaminated aqueous composition.

9. The method of claim 1, wherein said monitoring comprises monitoring contaminant characteristics of said aqueous composition within said well, wherein said well includes a probe and a sensor.

10. The method of claim 1, wherein said monitoring comprises sensing a contaminant and transmitting a signal concerning said contaminant from said well module to a data collector.

11. The method of claim 10, wherein said data collector collects said signal and transmits information concerning said contaminant derived from said signal.

12. The method of claim 11, wherein said collector transmits said information to a remote monitor.

13. The method of claim 12, wherein said information is transmitted over a web connection, phone modem connection, radio connection, network connection, wireless connection, cellular connection, satellite connection, Internet connection or combinations thereof.

14. The method of claim 12, further comprising outputting a contaminant report from said remote monitor.

15. The method of claim 1, comprising monitoring said treating of said aqueous composition in a plurality of groundwater extraction wells.

16. A system to treat a contaminated aqueous composition, comprising:

a capture zone to intercept said contaminated aqueous composition;

a surface pump and treat system to receive and treat said contaminated aqueous composition from said capture zone to remove a contaminant in said contaminated aqueous composition to a lower concentration than a concentration of said contaminant in said capture zone:

a sensor that senses said contaminant in said contaminated aqueous composition;

means comprising a monitor operable to receive information in real time concerning said contaminant from said sensor and to consequently control said pump and treat system to treat said contaminated aqueous composition;

wherein said monitor is situated at a location remote from said pump and treat system.

17. The system of claim 16, further comprising a sparger to sparge a non-reactive gas into said contaminated aqueous composition.

18. The system of claim 17, further comprising a diffuser to diffuse said contaminated aqueous composition through a membrane to separate a volatile contaminant wherein said volatile contaminant is sensed by said sensor.

19. The system of claim 16, further comprising a transmitter associated with said sensor to transmit a signal concerning said contaminant.

20. The system of claim 19, further comprising a collector to receive said signal from said transmitter.

21. The system of claim 20, wherein said collector is capable of transmitting a signal concerning said contaminant to said monitor.

22. The system of claim 21, further comprising a communication link that interconnects the data collector and the monitor, the communication link capable of transmitting said signal to enable a user at the monitor to obtain information concerning the contaminant.

23. The system of claim 22, wherein the communication link comprises a web connection.

24. The system of claim 22, wherein the communication link comprises a network.

25. The system of claim 22, wherein the communication link comprises a phone modem connection, radio communication connection, network communication connection, wireless communication system connection, cellular communication connection, satellite communication connection, web connection, Internet connection or combinations thereof.

26. The system of claim 22, further comprising a two-way communication between said collector and said sensor to permit selection, activation, de-activation, modification, fine-tuning, manipulation or resetting of said probe.

27. The system of claim 22, further comprising a communicator between said monitor and said pump and treat system to control said pump and treat system according to a signal from said monitor.

28. The system of claim 20, wherein the collector comprises a controller.

29. The system of claim 28, wherein the controller comprises a computer.

30. The system of claim 20, wherein the collector comprises a transceiver.

31. The system of claim 30, wherein the transceiver comprises an integrated antenna or a separate antenna.

32. The system of claim 16, wherein the sensor comprises an in-situ sensor, vapor sensor, chemical sensor, fiber optics sensor, solid-state sensor, metal oxide sensor, an electrochemical sensor or combinations thereof.

33. The system of claim 16, comprising a plurality of sensors to sense a contaminant.

* * * * *